US009500580B1

(12) United States Patent
Mitra et al.

(10) Patent No.: US 9,500,580 B1
(45) Date of Patent: Nov. 22, 2016

(54) GAS DETECTOR AND METHOD OF DETECTION

(71) Applicant: General Electric Company, Schenectady, NY (US)

(72) Inventors: Chayan Mitra, Bangalore (IN); Narendra Digamber Joshi, Schenectady, NY (US); Vinayak Tilak, Bangalore (IN); Gordon Raymond Smith, Ballston Spa, NY (US); Eric YuHang Fung, Houston, TX (US); Sandip Maity, Bangalore (IN); Rachit Sharma, Bangalore (IN); Steven Keith Handelsman, Cincinnati, OH (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 0 days.

(21) Appl. No.: 14/730,417

(22) Filed: Jun. 4, 2015

(51) Int. Cl.
 *G01N 21/3504* (2014.01)
 *G02B 27/14* (2006.01)
 *G01N 21/85* (2006.01)

(52) U.S. Cl.
 CPC ......... *G01N 21/3504* (2013.01); *G02B 27/141* (2013.01); *G01N 2021/8578* (2013.01)

(58) Field of Classification Search
 CPC ........... G01J 3/10; G02B 6/04; G02B 27/14; A61B 5/0062; G01N 21/3504
 See application file for complete search history.

(56) References Cited

U.S. PATENT DOCUMENTS

| | | | |
|---|---|---|---|
| 6,593,573 B1 | 7/2003 | McCann et al. | |
| 6,975,891 B2 * | 12/2005 | Pawluczyk | A61B 5/14532 250/339.12 |
| 6,975,975 B2 | 12/2005 | Fasca | |
| 7,005,645 B2 | 2/2006 | Von Drasek et al. | |
| 7,324,203 B2 | 1/2008 | Ho | |
| 7,787,728 B2 | 8/2010 | Masterson et al. | |
| 7,824,636 B1 | 11/2010 | Kraemer et al. | |
| 7,914,747 B1 | 3/2011 | Kraemer | |
| 8,151,571 B2 | 4/2012 | Maly et al. | |
| 8,244,505 B2 | 8/2012 | Headley et al. | |

(Continued)

FOREIGN PATENT DOCUMENTS

| | | |
|---|---|---|
| JP | 2007309800 A | 11/2007 |
| JP | 2012026918 A | 2/2012 |
| JP | 2013117517 A | 6/2013 |

OTHER PUBLICATIONS

Marini, "Siemens Flexible Generation for Renewable Integration", Jun. 11, 2012, retrieved from http://www.energy.ca.gov/2012_energypolicy/documents/2012-06-11_workshoppresentations/06_Marini_Siemens_2012_June11_CEC_Siemens.pdf on Nov. 5, 2015.

(Continued)

*Primary Examiner* — David Porta
*Assistant Examiner* — Faye Boosalis
(74) *Attorney, Agent, or Firm* — Douglas D. Zhang; GE Global Patent Operation

(57) ABSTRACT

A gas detector and method are presented. The gas detector includes a launcher unit for coupling and merging light beams in mid-infrared and infrared wavelength ranges into a single light beam and directing the merged single light beam towards a gas flow path; a receiver unit for generating at least one photo detector current signal based on the light beam transmitted through the gas flow path; and a control unit for processing at least one photo detector current signal to measure concentration of the at least two gases present in the gas flow path.

16 Claims, 7 Drawing Sheets

(56) References Cited

U.S. PATENT DOCUMENTS

| | | |
|---|---|---|
| 8,245,493 B2 | 8/2012 | Minto |
| 8,358,417 B2 | 1/2013 | Feitisch et al. |
| 8,411,267 B2 | 4/2013 | Normand |
| 8,424,292 B2 | 4/2013 | Hoyte et al. |
| 8,527,252 B2 | 9/2013 | Kephart et al. |
| 8,528,429 B2 | 9/2013 | Holt |
| 8,564,779 B2 | 10/2013 | Hara et al. |
| 8,711,340 B2 | 4/2014 | Maity et al. |
| 2004/0024541 A1 | 2/2004 | Uchida et al. |
| 2007/0168057 A1 | 7/2007 | Blevins et al. |
| 2008/0144677 A1 | 6/2008 | Belkin et al. |
| 2010/0091278 A1 | 4/2010 | Liu et al. |
| 2011/0130973 A1 | 6/2011 | Kimura |
| 2011/0174053 A1 | 7/2011 | Holt |
| 2012/0136483 A1 | 5/2012 | Haffner |
| 2012/0180548 A1 | 7/2012 | Bosselmann |
| 2012/0307241 A1 | 12/2012 | Maity et al. |
| 2013/0056626 A1 | 3/2013 | Shen et al. |
| 2013/0098462 A1 | 4/2013 | Hoskin |
| 2013/0209330 A1 | 8/2013 | Rahman et al. |
| 2013/0292571 A1 | 11/2013 | Mukherjee et al. |

OTHER PUBLICATIONS

Marra, "Siemens Advanced Hydrogen Turbine Development Program", UTSR 2012, Oct. 2, 2012, retrieved from http://www.netl.doe.gov/publications/proceedings/12/utsr/pdf/Marra.pdf on Nov. 5, 2015.

European Search Report and Opinion issued in connection with corresponding EP Application No. 15166609.6 on Oct. 16, 2015.

* cited by examiner

GAS DETECTOR AND METHOD OF DETECTION

BACKGROUND OF THE INVENTION

The invention relates generally to a gas detector and more particularly to a gas detector for power plant emission measurements and control.

Gas detectors have been used in various industrial applications such as power plants, transportation vehicles, gas turbines, and industrial, environmental, and biological processes and installations. A gas detector typically detects the presence of one or more gases in a given area. In some applications, detectors can further measure concentrations of specific gases.

In recent years, utility deregulation and increasing electrical demand have led to the integration of solar and wind power with combined cycle (CC) power plants. This integration has led to a desire to reduce start-up and shutdown times for the gas turbines in the CC power plants. The emission levels from a gas turbine vary depending on the manner in which the machine starts up or shuts down. Often, emissions from power plants may deteriorate as a result of seasonal changes, changes in fuel quality, and deterioration of gas turbine airfoils. A continuous emission measurement system (CEMS) comprising a gas detector measures gaseous emission species such as NOX (for example Nitrogen monoxide NO and Nitrogen dioxide NO2), carbon monoxide (CO) and ammonia (NH3) for continually demonstrating compliance to permitted emission limits.

A CEMS coupled with a gas detector typically uses an extractive process of sampling out near homogeneous portions of the exhaust gas from the exhaust gas duct, a heat recovery steam generator (HRSG) coupled to the exhaust gas duct, and a gas exhaust stack. This process typically requires from about 30 seconds to about 3 minutes of measurements as well as frequent purging and calibration processing. A CEMS typically uses measurement techniques such as interaction of light with the emission species like light absorption, chemi-luminescence, and/or non-dispersive infrared analysis. In light absorption based techniques, light beams of particular wavelengths, at which the respective emission species to be detected have peak absorption, are transmitted through an area where the emission species are expected to be present. One or more photo detectors then receive the transmitted light beams. Various types of photo detectors are available commercially and are chosen based on the wavelength of the light beams employed in detecting the gases. By employing Bear-Lambert's law and other correction and conversion factors, a controller can convert the photo detector output signal to provide concentration information of the specific gas or gases of interest and may further control and manage emissions.

Power generation plants require reliable, accurate, and timely detection and measurement of multiple gases. However, the harsh and challenging operating conditions of power generation plants may adversely affect selectivity and sensitivity in light absorption spectroscopy measurements. For example, during transient operations rapid changes of NOx levels can occur, and the CEMS technology will introduce a time delay in the NOx measurement. In such situations, ammonia injection may be incorrectly high or low depending on the actual NOx change during the time delay. A high ammonia injection in selective catalytic reduction (SCR) system leads to the formation of corrosive ammonium sulfates adversely impacting downstream hardware. A low ammonia injection in SCR system may lead to un-necessarily high stack NOx because not enough ammonia was injected when needed. In addition, many challenges exist for in-situ monitoring of power plant exhaust emission species such as the presence of moisture, harsh environment, high temperatures, and dynamic fluctuations in trace gas concentrations.

Accordingly, there is a need for simultaneous, in-situ, real time, selective, and sensitive measurement of multiple emission species to reduce and control startup and transient emissions in power plants. Further it would be desirable to provide reliable measurements with greater accuracy, repeatability, and consistency to demonstrate compliance or attainment to regulatory emission levels.

BRIEF DESCRIPTION OF THE INVENTION

In one embodiment, a gas detector for measuring concentration of at least two gases within a gas flow path includes a launcher unit which couples and merges light beams in mid-infrared and infrared wavelength ranges into a single light beam. A receiver unit generates at least one photo detector current signal based on the single light beam transmitted through the gas flow path. A control unit processes the at least one photo detector current signal to measure concentration of at least two gases present in the gas flow path.

In another embodiment, a gas detector for coupling mid-infrared and infrared light beams includes a first set of light sources for emitting light beams comprising a mid-infrared wavelength range and a second set of light sources which emit light beams comprising infrared wavelength ranges. First and second light transmission networks bundle the light beams in the mid-infrared and infrared wavelength ranges, respectively, for providing first and second bundled beams and then transmit the bundled beams towards a coupling unit. The coupling unit receives and couples the first and second bundled beams for providing a single coupled light beam. A receiver unit receives the single coupled light beam transmitted through a gas flow path.

In another embodiment, a method of detecting simultaneously at least two gases includes transmitting a first bundled light beam towards a coupling unit, wherein the first bundled light beam comprises a plurality of mid-infrared wavelengths with at least one of the plurality of mid-infrared wavelengths being different than another of plurality of mid-infrared wavelengths; transmitting a second bundled light beam towards the coupling unit, wherein the second bundled light beam comprises a plurality of infrared wavelengths with at least one of the plurality of infrared wavelengths being different than another of plurality of infrared wavelengths; receiving and coupling the first and second bundled light beams to produce a single coupled light beam; and transmitting the single coupled light beam through a gas flow path comprising the at least two gases.

DRAWINGS

These and other features, aspects, and advantages of the present invention will become better understood when the following detailed description is read with reference to the accompanying drawings, in which like characters represent like parts throughout the drawings, wherein.

DETAILED DESCRIPTION

Unless defined otherwise, technical and scientific terms used herein have the same meaning as is commonly understood by one of ordinary skill in the art to which this disclosure belongs. The terms "first", "second", and the like, as used herein do not denote any order, quantity, or importance, but rather are used to distinguish one element from another. Also, the terms "a" and "an" do not denote a limitation of quantity, but rather denote the presence of at least one of the referenced items. The term "or" is meant to be inclusive and mean one, some, or all of the listed items. The use of "including," "comprising" or "having" and variations thereof herein are meant to encompass the items listed thereafter and equivalents thereof as well as additional items. If ranges are disclosed, the endpoints of all ranges directed to the same component or property are inclusive and independently combinable. The modifier "about" used in connection with a quantity is inclusive of the stated value and has the meaning dictated by the context (e.g., includes the degree of error associated with measurement of the particular quantity).

Figure 1:
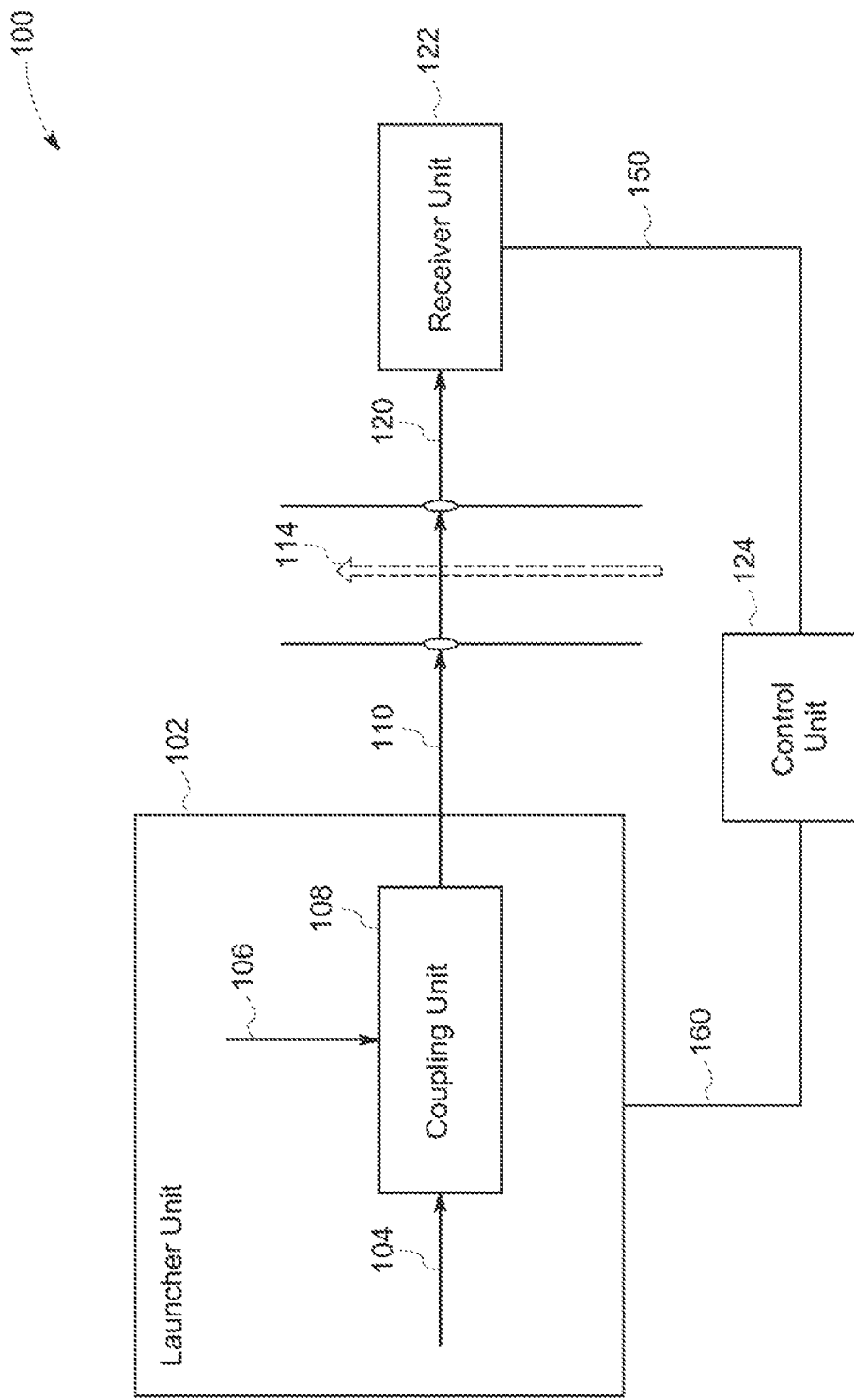
FIG. 1 is block diagram of a gas detection system in accordance with an embodiment of the invention.

FIG. 1 illustrates a gas detector 100 comprising a launcher unit 102 for coupling a light beam 104 in the mid-infrared (mid-IR) wavelength range with a light beam 106 in the infrared (IR) wavelength range in a coupling unit 108 for providing a coupled and merged single light beam 110 and directing the single light beam 110 towards a gas flow path 114. A receiver unit 122 collects the light beam 120 transmitted through the gas flow path, detects at least two gases present in the gas flow path 114, and generates one or more photo detector current signals 150. In more conventional embodiments wherein multiple light beams are transmitted through and received from a gas flow path, challenges associated with multiple light beams traveling through different regions in the gas flow path result in potential inaccuracies in measurements due to the turbulent transmission path and beam steering. Use of a single light beam, as described in this embodiment, removes such challenges, A control unit 124 processes the one or more photo detector current signals to measure concentrations of the at least two gases present in the gas flow path. Control unit 124 may further generate one or more driver current signals 160. In one embodiment, driver current signals 160 may be used to correct any misalignment of the launcher unit. Although a single control unit is shown as a separate block in FIG. 1 for purposes of illustration, in some embodiments, the control unit may comprise one or more units and may be situated in the receiver unit and/or the launcher unit.

Figure 2:
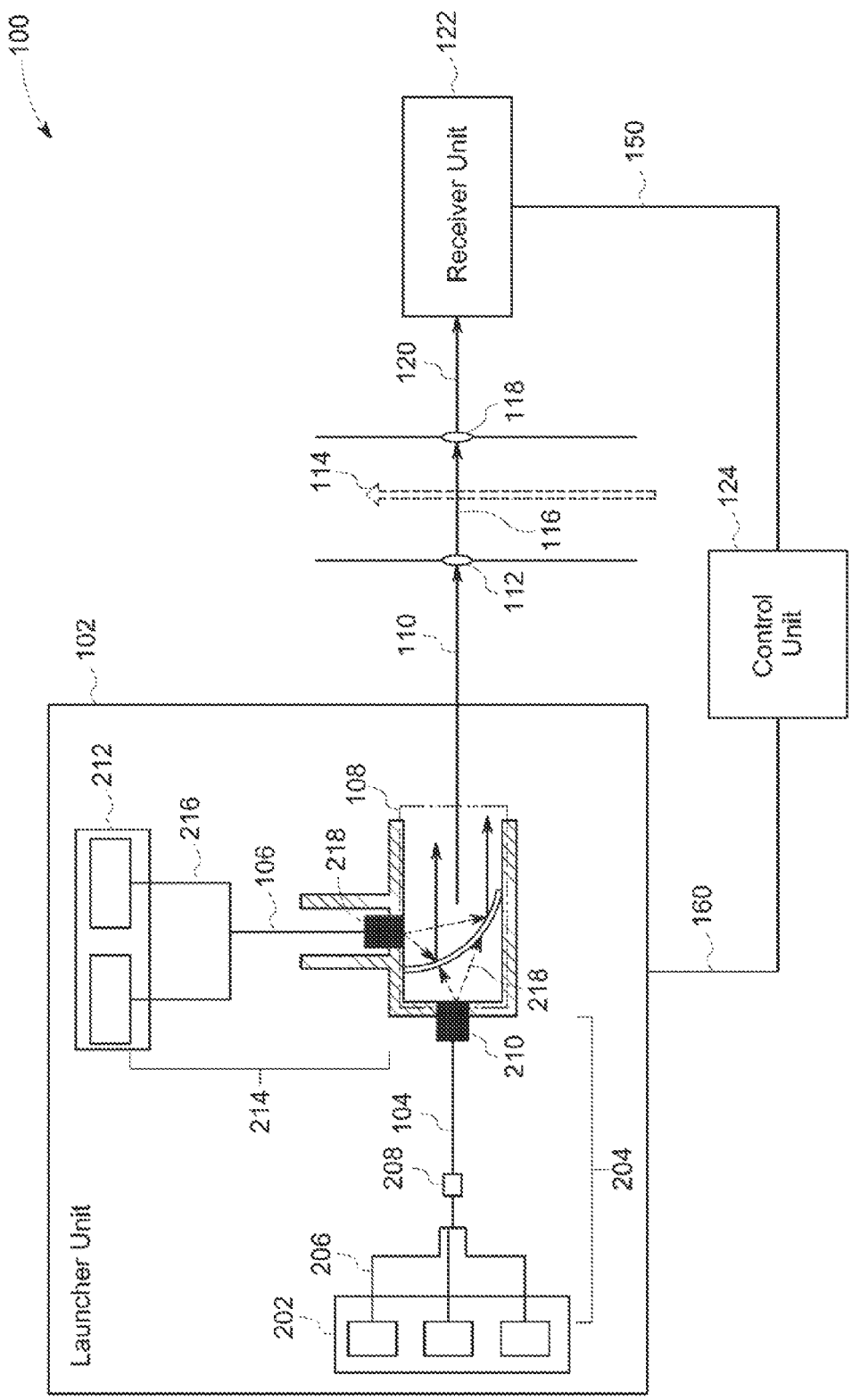
FIG. 2 is block diagram of a gas detection system in accordance with another embodiment of the invention.

In the more specific embodiment of FIG. 2, the launcher unit 102 further includes a first set of light sources 202 to emit light beams in the mid-infrared wavelength range, a first light transmission network 204 for bundling the light beams from the first set of light sources to produce a bundled first light beam 104 in the mid-IR wavelength range, a second set of light sources 212 to emit light beams in an infrared wavelength range, and a second light transmission network 214 for bundling the light beams from the first set of light sources to produce a bundled second light beam 106 in the IR wavelength range. The coupling unit 108 in the launcher unit merges the mid-IR and IR light beams 104 and 106 transmitted respectively through the first and second light transmission networks 204 and 214 into the single light beam 110. The single light beam 110 then is transmitted through a launching window 112 towards a gas flow path 114. The single light beam 110 interacts with gaseous species in the gas flow path as it travels through a path 116 inside the gas flow path and towards a receiving window 118. In one embodiment the interaction of the single light beam with gaseous species in the gas flow path includes light absorption. After interacting with the gaseous species, the single light beam 120 emerges from the receiver window and is transmitted towards the receiver unit 122. The receiver unit comprises photo detectors sensitive to specific wavelength ranges selected based on the requirement for detecting specific emission species. A control unit 124 receives photo detector current signals 150 from the receiver unit, uses the photo detector current signals to measure the emission species, and, in one embodiment, provides the driver current signal 160 to the first and second sets of light sources.

As used herein, "mid-infrared wavelength range" includes wavelengths ranging from about 3.5 µm to about 20 µm. Mid-IR light wavelength ranges in the electromagnetic radiation spectrum comprise absorption features of many molecules including water molecules and gaseous species in a gas turbine power plant such as nitrogen dioxide, nitrogen monoxide, carbon monoxide, and ammonia. In some embodiments, the first set of light sources for emitting mid-infrared light beams are configured such that one of the light beams has a different wavelength than at least one other of the light beams. For example, it is often desirable to simultaneously detect nitrogen dioxide and nitrogen monoxide, the most common gaseous emission species in a power plant, at two separate wavelengths to ensure selectivity and sensitivity. With respect to particular wavelengths of interest, nitrogen dioxide (NO2) may be detected near at least one of about 3.5 µm and about 6.3 µm, nitrogen monoxide (NO) may be detected near at about 5.3 µm, ammonia may be detected in the mid-IR wavelength range near at least one about 9 µm and about 10.4 µm, and carbon monoxide may be detected in the mid-IR wavelength range near 4.86 µm. In one embodiment two or more of such gases may be simultaneously detected such that one of the light sources transmits at a wavelength targeted towards a first gas and at least one other of the light sources transmits at a wavelength targeted towards at least one other gas.

In an exemplary embodiment, the first set of light sources 202 comprises a plurality of quantum cascade lasers (QCLs). Some of the advantages of such lasers include high optical power output of the order of several hundred milliwatts, broad tuning range, ability to operate at room temperature, large dynamic range, and failsafe operation combined with solid-state reliability. Quantum cascade lasers such as distributed feedback quantum cascade lasers (DFB-QCL) may be operated in a single mode allowing rapid scanning of a spectral wavelength range, resulting in gas detection measurement within about 1 second or within about 5 seconds. In a more specific embodiment, the first set of light sources 202 may include three QCLs emitting light beams at about 5.3 µm, about 6.3 µm and about 9 µm corresponding respectively to the peak absorption of nitrogen monoxide (NO), nitrogen dioxide (NO2) and ammonia (NH3). In an alternative embodiment, the first set of light sources 202 may include a single wavelength light source and a wavelength converter for converting the single wavelength light beam into a light beam comprising multiple mid-IR wavelengths.

As used herein, "infrared wavelength range" includes wavelengths ranging from about 0.8 µm to about 3 µm. Infrared (IR) light wavelength ranges of the electromagnetic radiation spectrum comprise absorption features of many molecules including water molecules and gaseous species in a power plant such as ammonia, carbon monoxide, and carbon dioxide. In some embodiments, second set of light sources 212 are configured for emitting infrared light beams with one of the light beams having a different wavelength than at least one other of the light beams. For example, the second set of light sources 212 may be configured for emitting one of the light beams near or at a peak absorption wavelength of carbon monoxide, and one other light beam near or at a wavelength insensitive to one or more emission gaseous species in the gas flow path. It is useful if the other wavelength is in additionally insensitive to water molecules. In one more specific aspect of this example, the second set of light sources 212 may be configured for emitting the one other light beam near or at a wavelength insensitive to carbon monoxide (CO) or water (H2O) molecules. In such embodiments, misalignments of the launcher and receiver units may be monitored as described in commonly assigned US20120307241. In an exemplary embodiment, the second set of light sources 212 may include a near-IR laser in a standard butterfly package, emitting light beam at about 2.3 µm corresponding to the peak absorption wavelength of carbon monoxide (CO) and one other light source in the second set emitting at about 1.3 µm, a wavelength at which the light absorption by both CO and H2O molecules is low. The second set of light sources 212 may include, for example, one or more of light emitting diodes, laser diodes, fabry-perot lasers, or any other portable light sources.

In some embodiments, the first light transmission network 204 may include light to fiber couplers (not shown) for coupling light beams from each of the first set of light sources 202 to an individual hollow-core optical fiber in the fiber optic network 206. In one embodiment, the first light transmission network may further include hollow core fibers bundled together for forming a bundled fiber 208. In some embodiments, the bundled fibers are coupled to a beam collimator 210 for enhancing beam convergence and for transmitting the bundled beams 104 towards a coupling unit 108. In an exemplary embodiment, the total length of the hollow-core fibers may be in the range of about 20 centimeters to about 30 centimeters.

In some embodiments, the second light transmission network 214 may include individual optical fibers 216 coupled to respective light source in the second set of light sources 212. In one embodiment, the optical fibers 216 are attached to a beam collimator 218 for enhancing beam convergence and for transmitting the light beams 106 from second set of light sources 212 towards a coupling unit 108 and beam collimators. In some embodiments, the second light transmission network may comprise a network similar to that of the first transmission network.

In one specific embodiment, the coupling unit 108 comprises a dichroic mirror. In an exemplary embodiment, the coupling unit comprises a semitransparent dichroic mirror to couple the mid-IR and IR light beams. As further examples, dichroic mirror 218 in the coupling unit may comprise a semitransparent planar mirror or a semitransparent parabolic mirror or any other semitransparent curved mirror. In the parabolic example, the semitransparent parabolic dichroic mirror 218 may receive the mid-IR light beams 104 and IR light beams 106 on its convex and concave surfaces respectively. As a result, the mid-IR light beams transmit through the semitransparent dichroic mirror and the IR light beams reflect, resulting in a single coupled and merged light beam 110 comprising both mid-IR and IR wavelengths.

Figure 3:
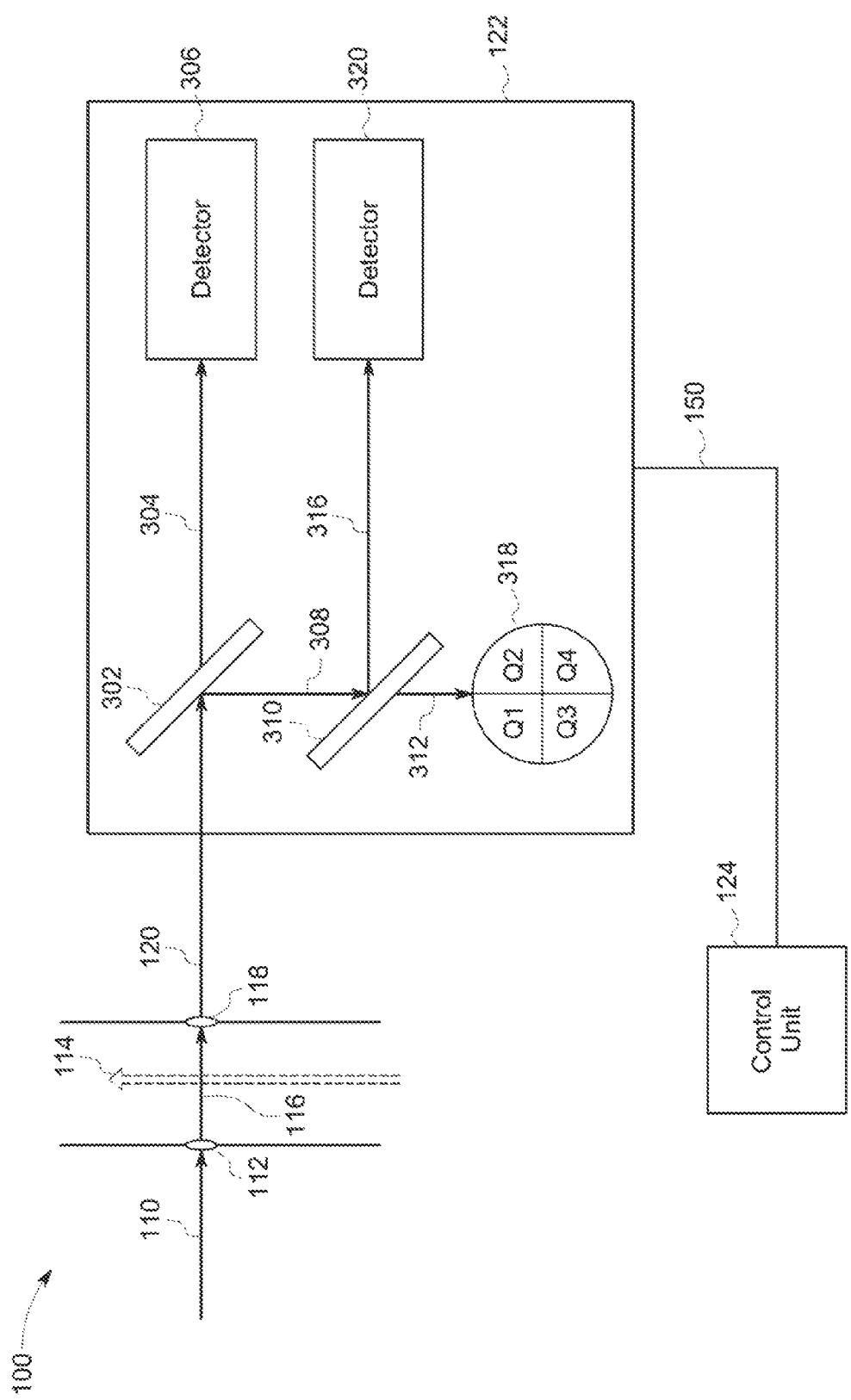
FIG. 3 is a block diagram of a receiver unit in accordance with another embodiment of the invention.

FIG. 3 illustrates an exemplary receiver unit 122 that receives the single coupled and merged beam 120 transmitted through the gas flow path. In one embodiment the receiver unit comprises a dichroic beam splitter 302 that receives the single coupled and merged beam 120. The dichroic beam splitter transmits a portion of the light beam 120 comprising mid-IR wavelengths 304 towards a mid-IR photo detector 306 and reflects another portion of the light beam comprising IR wavelengths 308 towards a second dichroic beam splitter 310. The second dichroic beam splitter 310 transmits a first light beam 312 towards a first IR photo detector 318 and reflects another light beam 316 having higher wavelength than the first light beam towards another IR photo detector 320.

In an exemplary embodiment, the dichroic beam splitter 302 comprises a Zinc Selenide (ZnSe) beam splitter, and the mid-IR photo detector 306 comprises a mercury-cadmium-telluride (MCT or Hg—Cd—Te) detector. In some embodiments, a chiller unit (not shown) may be attached to the mid-IR MCT detector for improving the detectivity and lowering the dark current of the detector. In an exemplary embodiment the MCT detector operates in a photovoltaic mode.

In an exemplary embodiment, the dichroic beam splitter 310 comprises a calcium fluoride (CaF) beam splitter, the IR photo detector 320 comprises a InGaAs photo detector, and the IR photo detector 318 comprises a silicon quad photo detector. In an exemplary embodiment, the light beam 312 comprises a monitor beam used for detecting and correcting launcher and receiver misalignments. In some other embodiments, which may be alternatives or in addition to the misalignment detection embodiment, the light beam 312 may detect issues with window fogging and/or be used to improve the signal to noise ratio of the gas detector.

In some embodiments, the control unit 124 includes a signal processing technique that processes the photo detector current signals for determining concentration of at least two gaseous emission species selected from a list comprising NO2, NO, CO and NH3. The concentrations may be determined using signal processing techniques such as for example, wavelength modulation spectroscopy, frequency modulation spectroscopy, and direct absorption spectroscopy as described in commonly assigned US20100091278A1. In some embodiments, the control unit 124 processes the photo detector current signals from the photo detectors 306, 310 and 320 and uses them to determine current drive signals for the launcher unit 102 (FIGS. 1-2).

Figure 4:
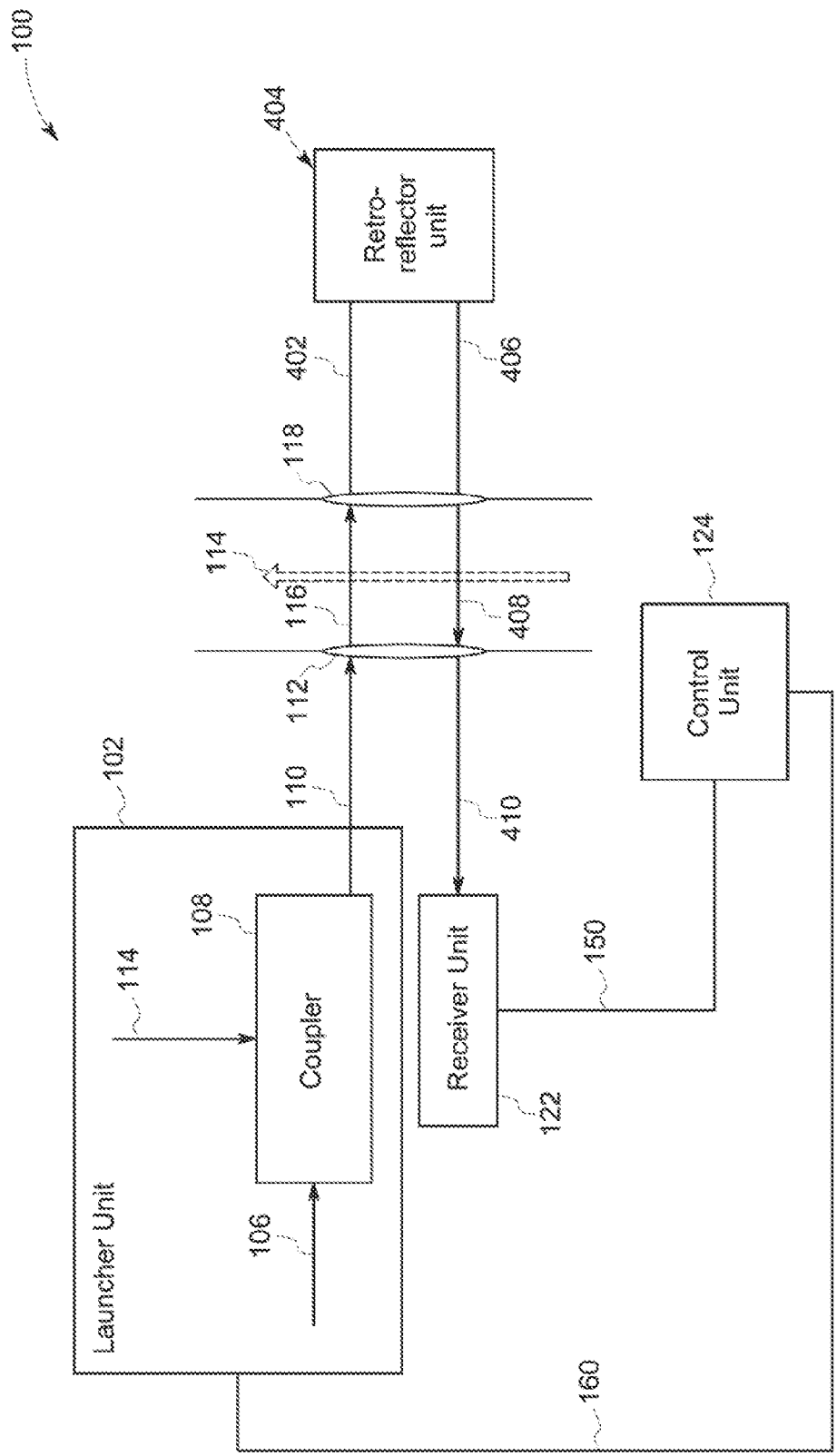
FIG. 4 is a block diagram in accordance with another exemplary embodiment of the present invention.

FIG. 4 illustrates an embodiment, wherein the launcher unit 102 and the receiver unit 122 are situated on a first side of the gas flow path, and a retro-reflector unit 404 is situated on a second side of the gas flow path opposite the first side. In this embodiment, the single light beam 110 interacts with gaseous species in the gas flow path as it travels through a path 116 inside the gas flow path and towards the window 118. After interacting with the gaseous species, the single light beam 402 emerges from the window 118 and is transmitted towards the retro-reflector 404 and undergoes more than two or more reflections in the retro-reflector 406. The light beam 406 emerges from the retroreflector after undergoing two or more reflections and travels through a gas flow path 408, before emerging from window 112. The receiver unit 122 receives the light beam 410 emerging out from window 112. This embodiment has the benefit of ease of situating most of the equipment on a single side of the gas flow path along with the challenges associated with potential additional noise and signal loss due to the turbulent transmission path and beam steering. In addition, situating the launcher and receiver units on the same side eases the challenges associated with misalignment of launcher and receiver units.

Figure 5:
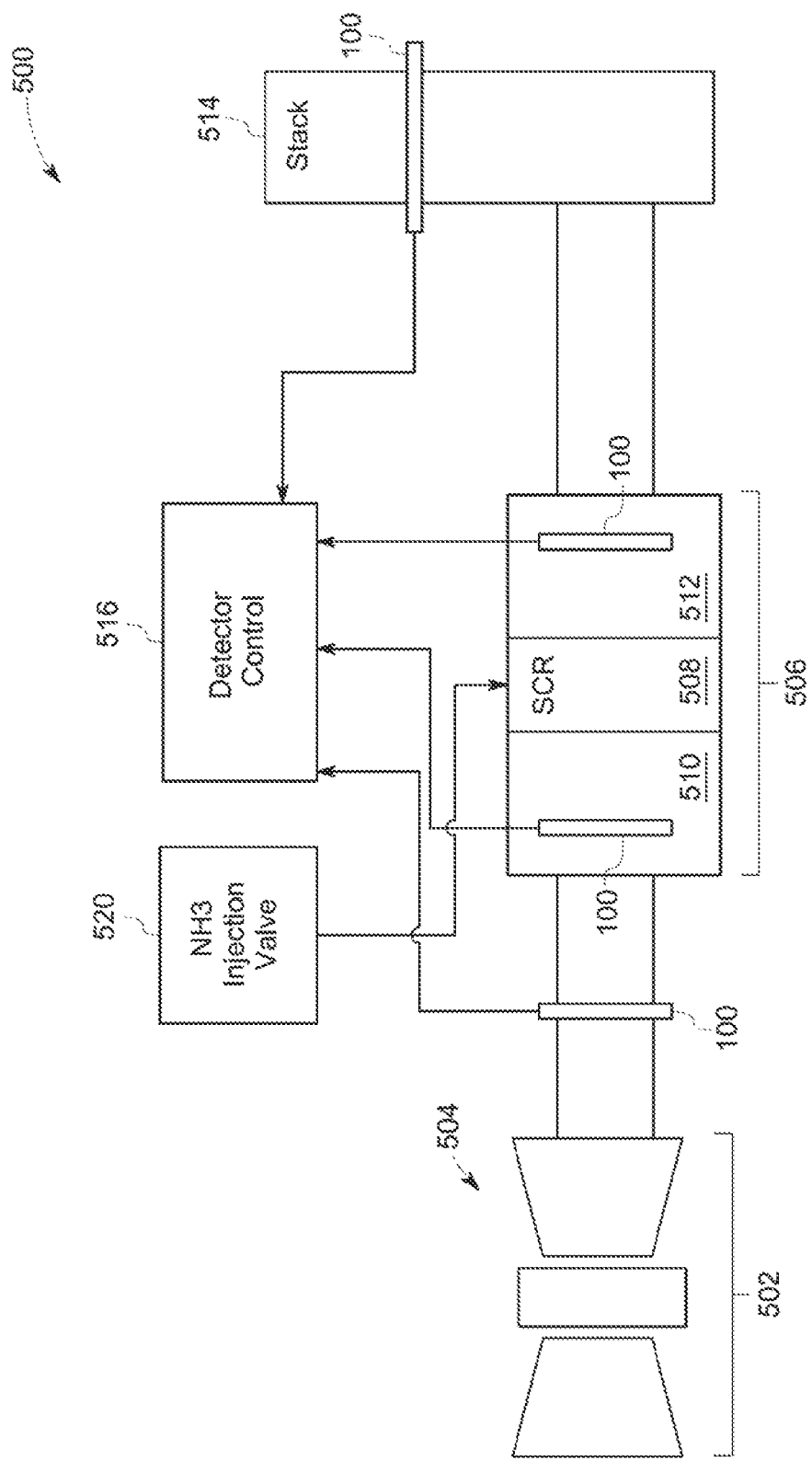
FIG. 5 is a. schematic representation of a gas turbine engine, a heat recovery steam generator (HRSG) with a selective catalytic reduction (SCR) system, and a control configuration according to an exemplary embodiment of the invention.

In power plants, continuous emission measurement systems (CEMS) comprising gas detectors measure and control gaseous emission species. FIG. 5 illustrates an embodiment comprising a gas turbine (GT) 502 and a gas exhaust duct 504 with a heat recovery steam generator (HRSG) 506. Some regions and states require that NOx emission from power plants be reduced to about 9-15 parts per million (ppm). It is often desirable to use catalysts in the form of selective catalytic reduction (SCR) system 508 in the HRSG to achieve these lower emission standards. In some embodiments, a plurality of gas detectors can detect concentration of gaseous species with a limit of detection as low as 1 ppm. In some embodiments, such as shown in FIG. 5, a plurality of gas detectors 100 may measure and control emission species within a gas flow path in one or more of gas turbine exhaust duct 502, inlet 510, and outlet 512 of the SCR system 508, and a gas turbine exhaust stack 514. In some other embodiments, the gas flow path being measured need not be directly in a gas turbine component. For example, some gas from one or more components may be directed to one or more sampling chambers (not shown) such that the gas flow path wherein the measurement occurs is in the one or more sampling chambers.

In a more specific embodiment, the gas flow path in the gas exhaust may comprise gaseous emission species including NO, NO2 and CO. In another specific embodiment the gas flow path at the inlet of the SCR system may comprise gaseous species including NO, NO2, NH3 and CO. In another specific embodiment in combination with or as an alternative to the aforementioned embodiment(s), the gas detector 100 may be used at the outlet 512 of SCR system 508 in HRSG 506. The gas flow path at the outlet of the SCR system may comprise at least two of the emission species NO, NO2, NH3 and CO. In one more specific embodiment, the gas flow path in the gas exhaust stack may comprise NO2, NO, NH3, CO and water molecules.

It is often desirable to operate catalysts in a narrow temperature range in which they efficiently reduce the targeted emission species such as NOx and CO. In an exemplary embodiment SCR 508 may employ NOx catalysts in a temperature range of about 600° F. to about 750° F. In another exemplary embodiment the temperature of the gas flow path within the exhaust gas duct may be up to about 1250° F. In yet another embodiment the temperature of the gas flow path within the exhaust stack may be about 70° F.

Figure 6:
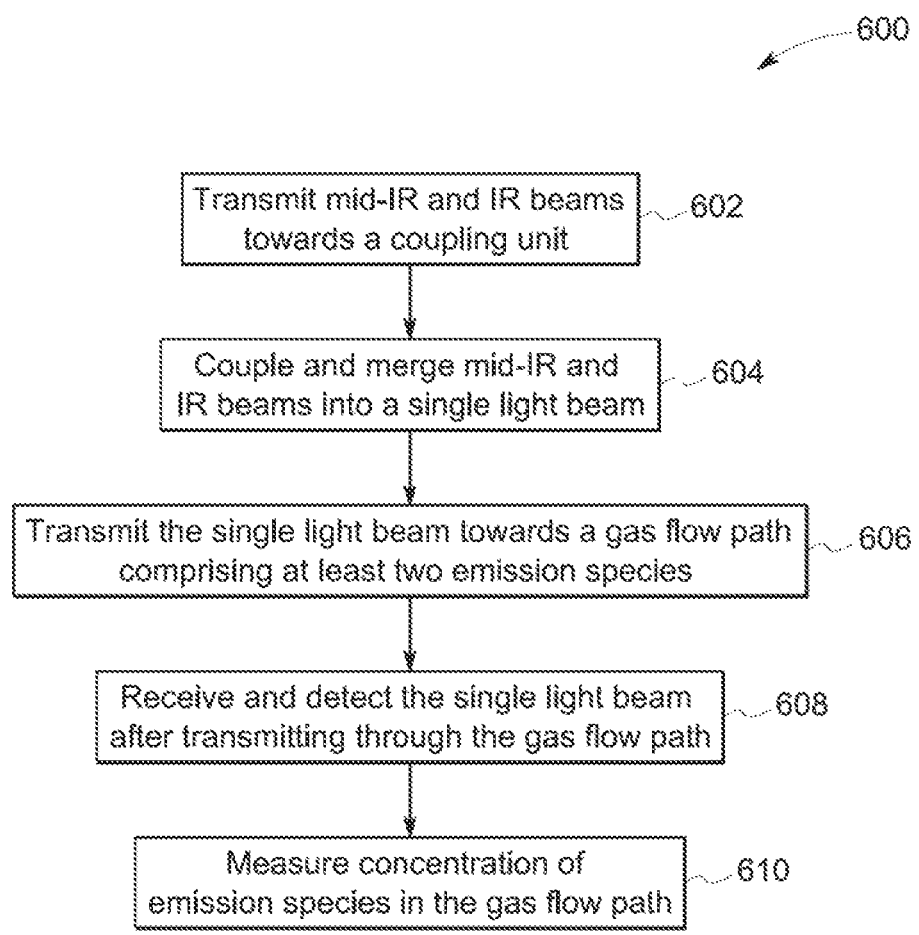
FIG. 6 is a flowchart of a gas detection method in accordance with one embodiment of the present invention.

FIG. 6 illustrates a gas detection method 600 for detecting simultaneously at least two gases. At step 602, a first light beam comprising at least one mid-IR wavelength and a second light beam comprising at least one IR wavelength are transmitted towards a coupling unit. At step 604 the first and second light beams are received and coupled to produce a single coupled light beam. Further, the gas detection method includes a step 606 for transmitting the single coupled light beam towards a gas flow path. The coupled light beam interacts with gaseous species in the gas flow path while being transmitted through the gas flow path. The method 600 further includes a step 608 for receiving and detecting the light beam transmitted in step 606. In some embodiments, the gas detection method further comprises a step 610 for analyzing the detected light beam and determining concentrations of at least two gases within the gas flow path. In an exemplary embodiment, the at least two gases comprise two or more gases selected from the group of NO2, NO, NH3 and CO. In another exemplary embodiment the at least two gases comprise at least NO2 and NO. In some embodiments, the gas flow path is within a gas turbine exhaust duct, a selective catalytic reduction system, or a gas turbine exhaust stack. In some other embodiments, the gas flow path is within a sampling chamber having gaseous species extracted from one or more of a gas turbine exhaust duct, a selective catalytic reduction system, or a gas turbine exhaust stack. In some embodiments, multiple detectors may be positioned within multiple gas paths. In some embodiments, the method may further comprise a step for controlling one or more combustion emission parameters based on the measured concentration of the at least two gases. In an exemplary embodiment, one or more combustion emission parameters may include one or more of fuel-to-air ratio, flow rates, and fuel distribution.

Generally, gas turbines exhaust gas contains about 8% to 10% of water molecules which often results in fogging of the launching and receiving windows due to water vapor present, which may attenuate the transmitted light beam. This may lead to errors in measurement methods by increasing the absorbed signal of the transmitted beam. Another source of error in gas measurement methods includes misalignment of launcher and receiver units over a period of time, resulting in loss of detector signal over a period of time. It is therefore often desirable to detect and correct fault conditions due to measurement errors such as misalignment of launcher and receiver units or window fogging. In some embodiments, the gas detection method 600 includes a method for detecting and correcting fault conditions as described in commonly assigned US20120307241A1, resulting in reliable detection of gases. In an exemplary embodiment, the fault condition may be due to one or both of window fogging and misalignment of launcher and receiver units.

It is often desirable to minimize current noise for reducing line widths of the emitted light beams. It is often also desirable to modulate the current drive signals to the first and second sets of light sources to enable lower detection limits. In one embodiment, the control unit 124 powers and drives the first and second sets of light sources. In one specific embodiment, the control unit 124 modulates the current driving signal 160 to the first and second sets of light sources. It is often desirable to tune wavelengths of light beams from one or more light sources in first and second sets of lights sources. A DFB QCL may be tunable by 0.002 μm/K. resulting in requiring a temperature stability of 0.0001 C to ensure wavelength stability. Any shift in temperature control of the laser will shift the wavelength to higher values. As a result, it is often useful to calibrate the wavelength emitted by light sources in both first and second sets of sources.

Figure 7:
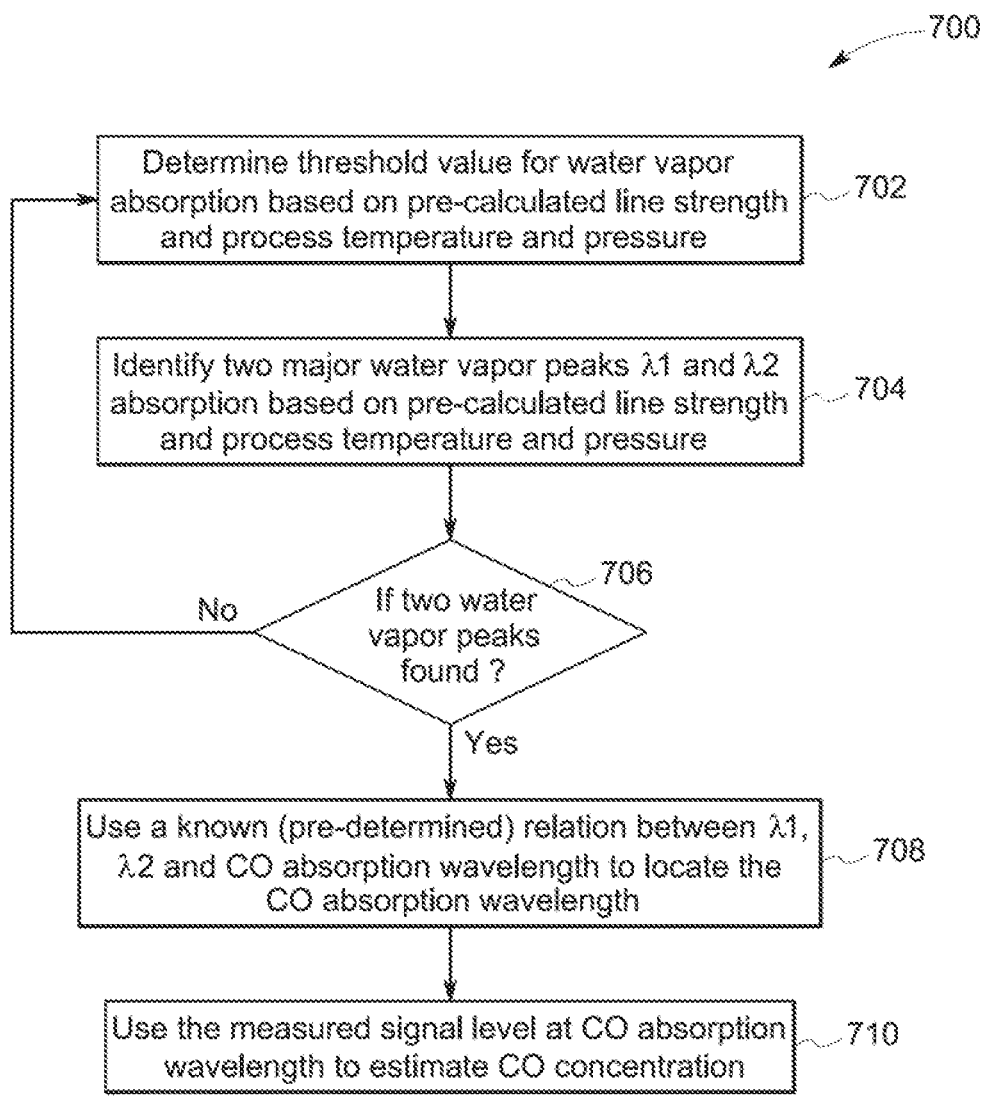
FIG. 7 is a flowchart of an example calibration method for carbon monoxide (CO) monitoring light source.

FIG. 7 illustrates an example calibration method 700 for calibrating the CO monitoring light source. At step 702, two major water vapor peaks $\lambda_1$ and $\lambda_2$ are identified such that the wavelength at which CO absorption peaks is in between $\lambda_1$ and $\lambda_2$. For example, the water vapor absorption transitions are at $\lambda_1$=2324 nm (4304.271 cm-1) and $\lambda_2$=2328 nm (4294.647 cm-1). At step 704, a pre-calculated line-strength for the water vapor lines using process temperature is used as a threshold value. For example, the pre-calculated line strength for a light source using process temperature is any value above the maximum detector current (or voltage) signal expected for the gaseous species being detected corresponding to the CO monitoring source. In step 706, in case one of the water molecule lines are not found, the light source is re-scanned with a wider scan range to locate the peaks. Once the water vapor peaks are identified, at step 708, the species peaks are located from the $\lambda_1$ peak, assuming the peak separation between the water molecules and the species peak remains same. At step 710, it is then validated with $\lambda_2$ peak of the water vapor. A similar method may be applied for calibrating each light source in the first and second sets of light sources.

While only certain features of the invention have been illustrated and described herein, many modifications and changes will occur to those skilled in the art. It is, therefore, to be understood that the appended claims are intended to cover all such modifications and changes as fall within the true spirit of the invention.

What is claimed is:

1. A gas detector comprising
a launcher unit comprising:
   a first set of light sources for emitting light beams in a mid-infrared wavelength range with one of the light beams having a different wavelength than at least one other of the light beams,
   a first light transmission network for bundling the light beams from the first set of light sources to produce a first bundled light beam,
   a second set of light sources for emitting light beams in an infrared wavelength range with one of the light beams having a different wavelength than at least one other of the light beams,
   a second light transmission network for bundling the light beams from the second set of light sources to produce a second bundled light beam, and
   a coupling unit for receiving and coupling the first and second bundled light beams to produce a single coupled light beam and for transmitting the coupled light beam towards a gas flow path; and
a receiver unit for receiving the coupled light beam after the coupled light beam has passed through the gas flow path;
wherein the coupling unit comprises a dichroic mirror;
wherein the dichroic mirror comprises a semitransparent dichroic mirror; and
wherein the dichroic mirror comprises a convex surface and a concave surface and receives one of the first and second bundled beams at the convex surface and the other of the first and second bundled beams at the concave surface.

2. The gas detector of claim 1, wherein the first set of light sources emit light beams at peak absorption wavelengths of at least two of NO2 (nitrogen dioxide), NO (nitric oxide or nitrogen monoxide) and NH3 (ammonia).

3. The gas detector of claim 1, wherein the second set of light sources is configured for emitting one of the light beams at a peak absorption wavelength of CO (carbon monoxide) and one other light beam at a wavelength insensitive to one or more emission gaseous species and water molecules in the gas flow path.

4. The gas detector of claim 1, wherein the gas flow path is within a gas turbine exhaust duct, a selective catalytic reduction unit, or a gas turbine exhaust stack.

5. The gas detector of claim 1, wherein the receiver unit comprises:
   a first dichroic beam splitter for receiving light beams having wavelengths in mid-infrared and infrared ranges transmitted through the gas flow path, transmitting the light beams in the mid-infrared wavelength range, and reflecting the light beams in the infrared wavelength range, and
   a second dichroic beam splitter for receiving the light beams in the infrared wavelength range reflected from the first dichroic beam splitter, transmitting a first light beam, and reflecting another light beam having a higher wavelength than the wavelength of the first light beam.

6. The gas detector of claim 5, further comprising a control unit, wherein the control unit processes photo detector current signals generated by the receiver unit to measure concentrations of constituent gases in the gas flow path.

7. A method for simultaneously detecting at least two gases, the method comprising:
   transmitting a first bundled light beam towards a coupling unit, wherein the first bundled light beam comprises a plurality of mid-infrared wavelengths with at least one of the plurality of mid-infrared wavelengths being different than another of plurality of mid-infrared wavelengths;
   transmitting a second bundled light beam towards the coupling unit, wherein the second bundled light beam comprises a plurality of infrared wavelengths with at least one of the plurality of infrared wavelengths being different than another of plurality of infrared wavelengths;
   receiving and coupling the first and second bundled light beams to produce a single coupled light beam utilizing a coupling unit;
   transmitting the single coupled light beam through a gas flow path comprising the at least two gases;
   receiving and detecting the coupled light beam after the coupled beam is transmitted through the gas flow path; and
   analyzing the detected light beam to determine concentrations of the at least two gases within the gas flow path;
   wherein the coupling unit comprises a dichroic mirror;
   wherein the dichroic mirror comprises a semitransparent dichroic mirror; and
   wherein the dichroic mirror comprises a convex surface and a concave surface and receives one of the first and second bundled beams at the convex surface and the other of the first and second bundled beams at the concave surface.

8. The method of claim 7, wherein determining the concentrations of the at least two gases further comprises at least one of wavelength modulation spectroscopy, frequency modulation spectroscopy or direct absorption spectroscopy.

9. The method of claim 7, wherein determining the concentrations of the at least two gases further comprises calibrating the wavelength emitted by light source corresponding to each of the gaseous species being measured.

10. The method of claim 7, further comprising controlling one or more combustion emission parameters based at least in part on the concentration of the at least two gases.

11. The method of claim 7, wherein the at least the two gases comprise NO2 (nitrogen dioxide) and NO (nitric oxide or nitrogen monoxide).

12. The method of claim 11, further comprises detecting at least one of CO (carbon monoxide) and NH3 (ammonia).

13. A gas detector comprising:
- a launcher unit for coupling and merging light beams in mid-infrared and infrared wavelength ranges into a single light beam and directing the merged single light beam towards a gas flow path;
- a receiver unit for generating at least one photo detector current signal based on the light beam transmitted through the gas flow path; and
- a control unit for processing at least one photo detector current signal to measure concentration of the at least two gases present in the gas flow path;
- wherein the launcher and receiver units are situated on a first side of the gas flow path, and wherein the gas detector further comprises:
- a retro-reflector unit situated on a second side of the gas flow path opposite the first side for receiving the light beam transmitted through the gas flow path and re-transmitting the received beam through the gas flow path before the received beam is collected at the receiver unit.

14. The gas detector of claim 13, wherein the ambient temperature of the gas flow path is between about 70° F. to about 1250° F.

15. The gas detector of claim 13, wherein the limit of detection for concentration measurement is as low as about 1 ppm.

16. A continuous emission monitoring system comprising the gas detector of claim 13.

* * * * *